United States Patent
Gu et al.

(10) Patent No.: US 9,474,916 B2
(45) Date of Patent: Oct. 25, 2016

(54) CARBAMATES FROM GLYCERINE CARBONATE FOR PEARLIZATION

(71) Applicant: Evonik Industries AG, Essen (DE)

(72) Inventors: Bin Gu, State College, PA (US); Brajesh Jha, Midlothian, VA (US); Sithamalli Chandramouli, Madison, WI (US); Jie Yang, Madison, WI (US)

(73) Assignee: Evonik Degussa GmbH, Essen (DE)

( * ) Notice: Subject to any disclaimer, the term of this patent is extended or adjusted under 35 U.S.C. 154(b) by 96 days.

(21) Appl. No.: 14/450,388

(22) Filed: Aug. 4, 2014

(65) Prior Publication Data

US 2015/0044264 A1 Feb. 12, 2015

Related U.S. Application Data

(60) Provisional application No. 61/863,596, filed on Aug. 8, 2013.

(51) Int. Cl.
| | |
|---|---|
| *A61K 8/42* | (2006.01) |
| *A61Q 19/10* | (2006.01) |
| *A61Q 5/02* | (2006.01) |
| *A61Q 5/12* | (2006.01) |
| *C11D 3/32* | (2006.01) |
| *A61K 8/49* | (2006.01) |
| *C11D 3/00* | (2006.01) |
| *C11D 7/32* | (2006.01) |

(52) U.S. Cl.
CPC ............ *A61Q 19/10* (2013.01); *A61K 8/42* (2013.01); *A61K 8/498* (2013.01); *A61K 8/4973* (2013.01); *A61Q 5/02* (2013.01); *A61Q 5/12* (2013.01); *C11D 3/0089* (2013.01); *C11D 3/32* (2013.01); *C11D 7/3263* (2013.01); *A61K 2800/412* (2013.01)

(58) Field of Classification Search
CPC ............ A61K 8/44; A61K 2800/412; C11D 3/0089; C11D 7/3263; C07C 271/16
See application file for complete search history.

(56) References Cited

U.S. PATENT DOCUMENTS

| | | | |
|---|---|---|---|
| 5,091,543 A | 2/1992 | Grey | |
| 5,430,866 A | 7/1995 | Lawrence et al. | |
| 5,646,106 A | 7/1997 | Chen et al. | |
| 5,925,604 A | 7/1999 | Chen et al. | |
| 6,025,504 A | 2/2000 | Claude et al. | |
| 6,165,955 A | 12/2000 | Chen et al. | |
| 7,578,995 B2 | 8/2009 | Frantz et al. | |
| 8,017,719 B2* | 9/2011 | Bernard | C08G 71/04 525/462 |
| 2004/0110659 A1 | 6/2004 | Herault et al. | |
| 2004/0119659 A1* | 6/2004 | Justice | G06F 3/0489 345/1.1 |

FOREIGN PATENT DOCUMENTS

| | | |
|---|---|---|
| DE | 4029232 A1 | 3/1992 |
| DE | 4117033 A1 | 11/1992 |
| EP | 582201 A2 | 10/1994 |
| EP | 955298 B1 | 2/2000 |
| EP | 2174937 B1 | 4/2015 |
| JP | 06329663 A | 11/1994 |
| JP | 2007/039347 A | 2/2007 |
| WO | WO2009035269 A2 | 3/2009 |

OTHER PUBLICATIONS

Hursthouse et al. Organic Process Research & Development, Why Do Organic Compounds Crystallize Well or Badly or Ever so Slowly? Why is Crystallization Nevertheless Such a Good Purification Technique?, 2009, 13, 1231-1240.*
Bolzinger, M.A. et al. "Effects of surfactants on crystallization of ethylene glycol distearate in oil-in-water emulsion" Colloids and Surfaces A, Physicochem and Engineering Aspects, ScienceDirect, vol. 299, 2007, pp. 93-100.
Sonnati, M. et al. "Glycerol carbonate as a versatile building block for tomorrow: synthesis, reactivity, properties and applications," Green Chemistry, vol. 15, pp. 283-306.

* cited by examiner

*Primary Examiner* — Paul A Zucker
(74) *Attorney, Agent, or Firm* — Linda S. Li; Jason S. Ngui; Bernard Lau

(57) ABSTRACT

Alkyl and/or alkenyl glycerol carbamate prepared by reacting a carbonate selected from the group consisting of glycerol carbonate, diglycerol carbonate, polyglycerol carbonate and mixtures thereof, with an amine of the general formula (I):

$$HNR^1R^2 \qquad (I)$$

wherein $R^1$ represents a hydrogen atom or a hydrocarbon group selected from the group consisting of alkyl groups and alkenyl groups having from 1 to 22 carbon atoms and $R^2$ represents a hydrocarbon group selected from the group consisting of alkyl groups and alkenyl groups having from 4 to 22 carbon atoms, and cyclic alkyl groups having 5 or 6 carbon atoms, are described along with methods for their use as pearlizing agents in surface-active preparations.

7 Claims, No Drawings

US 9,474,916 B2

CARBAMATES FROM GLYCERINE CARBONATE FOR PEARLIZATION

This application is a Non-Provisional application under 35 U.S.C. 119(e) which claims the benefit of U.S. Patent Application No. 61/863,596 filed on Aug. 8, 2013.

FIELD OF THE INVENTION

The present invention relates to glycerol carbamates which can be obtained by reaction of glycerol, diglycerol, and/or polyglycerol carbonate with primary and/or secondary amines, to a process for their production, and their use as pearlizing agents.

BACKGROUND OF THE INVENTION

Pearlizing agents are routinely added to personal care and household products to make the products pearly and silky. Ethylene glycol distearate or monostearate are commonly used pearlizing agents. These pearlizing agents generally do not have viscosity building effect; therefore, additional thickeners are needed in the formulation to prevent the formulation from becoming just an emulsion.

To generate a pearlizing effect, the pearlizing agents also need to have the appropriate crystal size, which are generally in microns. However, the ability to control the crystal size is limited. In using these pearlizing agents, the formulation is typically heated first to solubilize the pearlizing agents. Afterwards, the formulation is cooled down for the pearlizing agents to crystallize. In the heating step, the right solubilizing concentration needs to be used. If the solubilizing concentration is too high or too low, crystallization may not occur. In the cooling step, the cooling rate, flow rate and other parameters need to be monitored in order for the pearlizing agents to crystallize to the appropriate size. If the cooling rate is too fast, crystals may form too quickly and grow too large in size. If the cooling rate is too slow, the processing time will be prolonged, which will increase production costs. The stirring speed also needs to be controlled. During the solubilizing stage, at high temperatures fast stirring should be employed so the pearlizing agent can dissolve quickly. At the cooling stage, low stirring speed is preferred to help the crystallization process. The choice of surfactants can also affect the crystal formation and therefore the pearlizing effect. (Bolzinger et. al., *Colloids and Surfaces A*, Physicochemical and Engineering Aspects, 2007, 299, 93). Overall the process can be complicated and can result in inconsistencies in crystal size formation, and failure in generating a pearlizing effect.

Several methods have been introduced to overcome the problem. For example, a dispersion of ethylene glycol distearate in water is commercially available (Tego Pearl N 100, Tego Pearl N 300, Evonik Goldschmidt Corporation). These pearlizing agents can be used at room temperature without the need to heat the formulation. However, when the final formulation viscosity is low, the pearlizing agent can precipitates out of the system. Therefore, thickeners need to be added, which can increase the formulation cost.

Pearlizing concentrates were also mentioned in U.S. Pat. Nos. 5,646,106; 5,925,604; 6,165,955; and 7,578,995. The concentrates consist of ethylene glycol stearates, non-ionic surfactant (ethoxylated fatty alcohol), amphoteric surfactant (betain), glycol emulsifier and water. Such concentrates can be formulated with other ingredients at room temperature to generate a formulation with pearlizing effect. However, such a formulation does not have a good viscosity building effect. Cocamide diethanol amine (cocamide DEA) and other thickeners need to be added. Furthermore, the concentrate contains ethoxylated fatty alcohol, which limits their use in polyethylene glycol free applications.

Pearlizing concentrates were also mentioned in U.S. Patent Publication No. 20040110659, which described glycerol carbamates made by reaction of glycerol, diglycerol and/or polyglycerol carbonate with a primary and/or secondary amine. Such carbamates were found to be thickeners for cosmetic and pharmaceutical preparations. The materials were prepared by addition of fatty amines to glycerol carbonates. The hydrophilic impurities were removed by dichloromethane and extracted with hydrochloric acid. However, for cosmetic applications, dichloromethane is a toxic solvent, and its use should be avoided.

As such there is a need in the art for a pearlizing agent that is easy to use and that can be cost efficient in developing formulations. It is a further object of the present invention to provide a pearlizing agent that displays a viscosity building effect. These needs are satisfied by the present invention.

SUMMARY OF THE INVENTION

In accordance with the purposes of the disclosed materials, compositions, articles, devices, and methods, as embodied and broadly described herein, the disclosed invention, in one aspect, relates to use of alkyl and/or alkenyl glycerol carbamates obtainable by reaction of glycerol, diglycerol and/or polyglycerol carbonate with a primary and/or secondary amine as pearlizing agents in surface-active preparations. Surface-active preparations in the context of the invention are preferably cosmetic and/or pharmaceutical preparations, laundry detergents, dishwashing detergents and household cleaners.

In another aspect, the invention relates to pearlizing isomeric mixtures of alkyl and/or alkenyl glycerol carbamates that can be used in compositions of surface-active preparations.

In another aspect, the invention relates to a process for preparing alkyl and/or alkenyl glycerol carbamates obtainable by reaction of glycerol, diglycerol and/or polyglycerol carbonate with a primary and/or secondary amine without using dichloromethane, hydrochloric acid, or other harsh chemicals as a solvent. The process is a one step reaction excluding the use of solvents and extraction steps. The material obtained can be used immediately after it is prepared, thereby reducing manufacturing costs. More importantly, the carbamates of the present invention were found to have pearlizing effects in surface-active preparations.

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION OF THE INVENTION

Before the present compounds, isomer mixtures, and processes are disclosed and described, it is to be understood that the aspects described herein are not limited to specific processes, compounds, synthetic methods, articles, devices, or uses as such can, of course, vary. It is also to be understood that the terminology used herein is for the purpose of describing particular aspects only and, unless specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "wt. %" or "weight percent" or "percent by weight" of a component, unless specifically stated to the contrary, refers to the ratio of the weight of the component to the total weight of the composition in which the component is included, expressed as a percentage.

As used herein, the term "molecular weight," unless otherwise specified, refers generally to the relative average molecular weight of the bulk polymer. In practice, molecular weight can be estimated or characterized in various ways including gel permeation chromatography (GPC) or capillary viscometry. GPC molecular weights are reported as the weight-average molecular weight (Mw) or as the number-average molecular weight (Mn). Capillary viscometry provides estimates of molecular weight as the Inherent Viscosity (IV) determined from a dilute polymer solution using a particular set of concentration, temperature, and solvent conditions.

As used herein, the term "pearlizing effect," means providing a pearly appearance that imparts iridescent sheen or glow.

As used herein, the term "alkyl" is defined to include saturated aliphatic hydrocarbons including straight chains and branched chains. Preferably, the alkyl group has 8 to 22 carbon atoms.

As used herein, the term "alkenyl" is defined to include aliphatic hydrocarbons having at least one carbon-carbon double bond, including straight chains and branched chains having at least one carbon-carbon double bond. Preferably, the alkenyl group has 8 to 22 carbon atoms.

As used herein, the term "alkynyl" is defined to include aliphatic hydrocarbons at least one carbon-carbon triple bond, including straight chains and branched chains having at least one carbon-carbon triple bond. Preferably, the alkynyl group has 8 to 22 carbon atoms.

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the following detailed description are exemplary and explanatory only and are not restrictive.

The present invention relates to alkyl and/or alkenyl glycerol carbamates which are obtainable by reaction of glycerol, diglycerol and/or polyglycerol carbonate with a primary and/or secondary amine corresponding to Formula (I):

$$HNR^1R^2 \qquad (I)$$

in which $R^1$ is H or a linear and/or branched alkyl and/or alkenyl group containing 1 to 22 carbon atoms and $R^2$ is a linear and/or branched alkyl and/or alkenyl group containing 4 to 22 carbon atoms or a cyclic alkyl group containing 5 or 6 carbon atoms.

The present invention also relates to a process for the production of alkyl and/or alkenyl glycerol carbamates in which glycerol, diglycerol and/or polyglycerol carbonate is/are reacted with a primary and/or secondary amine corresponding to Formula (I):

$$HNR^1R^2 \qquad (I)$$

in which R is H or a linear and/or branched alkyl and/or alkenyl group containing 1 to 22 carbon atoms and $R^2$ is a linear and/or branched alkyl and/or alkenyl group containing 4 to 22 carbon atoms or a cyclic alkyl group containing 5 or 6 carbon atoms. The process involves addition of the primary and/or secondary amine into glycerol, diglycerol and/or polyglycerol carbonates and heating the reaction mixture at a temperature of 50-90° C. The mixture was then cooled down to room temperature, and the product was used without additional extraction or purification steps.

The alkyl and/or alkenyl glycerol carbamates of the present invention that have chiral centers may exist as stereoisomers, such as racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. The alkyl and/or alkenyl glycerol carbamates of the present invention may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety. Suitable stereoselective techniques are well-known to those of ordinary skill in the art.

It has surprisingly been found that alkyl and/or alkenyl glycerol carbamates are suitable as pearlizing agents for a broad range of surface-active preparations and that the pearlizing effect, for example in cosmetic and/or pharmaceutical preparations, is obtained by addition of only small quantities of the carbamates. At the same time, they are readily biodegradable and can be produced by simple reaction of glycerol, diglycerol and/or polyglycerol carbonate with primary or secondary amines. The alkyl and/or alkenyl glycerol carbamates of the present invention may also have viscosity building effect.

To generate this pearlizing effect, the pearlizing agent, which may contain the pearlizing compound, pearlizing isomeric mixture, or pearlizing composition, needs to form crystals in the surface-active preparations. In one embodiment, the size of the crystals can range from 0.1 micron to 500 microns, preferably 1 micron to 200 microns, even more preferably 4 microns to 100 microns. The formation of crystals is affected by various factors that include the concentration of the pearlizing agents, the type of surfactants used, and the processing parameters for forming the alkyl and/or alkenyl glycerol carbamates. These parameters include the heating and cooling rate, and the speed of stirring the reaction. For example, during the cooling stage a low stirring speed is generally preferred to facilitate the crystallization process. Very high stirring speed will disrupt with crystal formation, and may lead to an opaque instead of pearlescent preparation. During the solubilizing stage, at high temperatures fast stirring should be employed so the pearlizing agent can dissolve quickly. The type of surfactant affects the solubility of the pearlizing agent, which in turn affects the crystal formation rate, and thereby the pearlizing effect in the preparation.

In order to observe the pearlizing effect described in this invention, the mean crystal size needs to be in a controlled range. In one embodiment, the mean crystal size is in the range from 0.1 micron to 500 microns, preferably 1 micron to 200 microns, even more preferably 4 microns to 100 microns. In one embodiment, the concentration of the carbamate pearlizing agent in the formulation is 0.01-10.0%, preferably 0.5-4%. The concentration of active surfactant is 3-30%, preferably 8-20%. The formulation is heated to a temperature of about 60-90° C., preferably 65-80° C. The formulation is heated until the carbamate is completely dissolved. The formulation is then cooled down to room temperature under low stirring speed. For example, if making a 500 g lab batch, a lower than 150 rpm stirring speed is preferred with an overhead stirrer.

The crystal size can be measured by typical particle size analyzer instruments, such as but not limited to Beckman Coulter LS 13 320 Laser Diffraction Particle Size Analyzer. The formulations containing the alkyl and/or alkenyl glycerol carbamates according to the invention were diluted with water so the carbamate concentration is at around 0.5 wt %. The samples were measured at 25° C. at a pump speed 50%, obscuration 8% and sample density 1 g/ml. The Fraunhofer theory was used to calculate the crystal size distribution. The calculations were performed using the LSI 13 320 software (version 5.01): Universal Liquid Module.

In addition to having the appropriate crystal size, the crystals also need to be stable in the preparation. To maintain stability of the crystals, the preparation can be prepared at a certain viscosity. In one embodiment, the formulation has a viscosity that is preferably 1,000 cps and above.

Alkyl and/or Alkenyl Glycerol Carbamates

According to the invention, the alkyl and/or alkenyl glycerol carbamates used are obtained by reaction of glycerol, diglycerol and/or polyglycerol carbonate, preferably glycerol and/or diglycerol carbonate and, more particularly, glycerol carbonate, with a primary and/or secondary amine corresponding to Formula (I):

$$HNR^1R^2 \quad (I)$$

in which $R^1$ is H or a linear and/or branched alkyl and/or alkenyl group containing 1 to 22, preferably 6 to 18 and more particularly 8 to 16 carbon atoms and $R^2$ is a linear and/or branched alkyl and/or alkenyl group containing 4 to 22, preferably 6 to 18 and more particularly 8 to 16 carbon atoms or a cyclic alkyl group containing 5 or 6 and preferably 6 carbon atoms, more particularly a linear and/or branched alkyl and/or alkenyl group containing 1 to 22, preferably 6 to 18 and more particularly 8 to 16 carbon atoms.

Glycerol carbonate is:

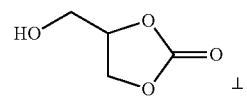

Diglycerol carbonate is a mixture of:

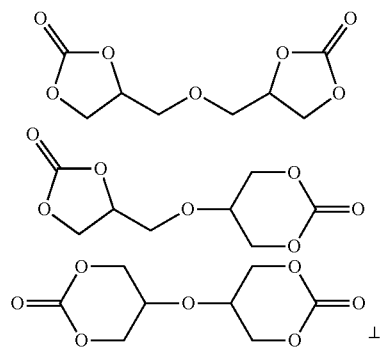

The compounds used in the reaction with polyglycerol carbonates have a molecular weight of preferably 200 to 1,000, more preferably 300 to 800 and most preferably 400 to 700 g/mol and contain preferably 2 to 9.2, more preferably 3 to 8 and most preferably 4 to 7 mmol $CO_2$ per g polyglycerol carbonate. The latter characteristic is a coulometric quantitative determination of organic carbonates by modification to DIN 18 129. A sample of the carbonate is weighed in, hydrolyzed for 1 h at 50° C. with a 1.4 M NaOH 15:1 methanol/water solution and the quantity of $CO_2$ released by acidification is determined using a carbon dioxide analyzer (UIC Model CM 140 or an equivalent instrument).

One particular embodiment of the present invention is characterized by the use of alkyl and/or alkenyl glycerol carbamates which are obtained by reaction of glycerol and/or diglycerol carbonate with a primary and/or secondary amine corresponding to formula (I), in which $R^1$ is H or a linear and/or branched alkyl and/or alkenyl group containing 1 to 22, preferably 6 to 18 and more particularly 8 to 16 carbon atoms and $R^2$ is a linear and/or branched alkyl and/or alkenyl group containing 4 to 22, 1 to 22, preferably 6 to 18 and more particularly 8 to 16 carbon atoms or a cyclic alkyl group containing 5 or 6 carbon atoms.

Another preferred embodiment of the present invention is characterized by the use of alkyl and/or alkenyl glycerol carbamates which are obtained by reaction of glycerol and/or diglycerol carbonate with a primary and/or secondary amine corresponding to formula (I), in which $R^1$ is H and $R^2$ is a linear and/or branched alkyl and/or alkenyl group containing 4 to 22 carbon atoms or a cyclic alkyl group containing 5 or 6 carbon atoms and preferably a linear and/or branched alkyl and/or alkenyl group containing 6 to 18 and more particularly 8 to 16 carbon atoms.

A particular embodiment of the invention is characterized by the use of alkyl and/or alkenyl glycerol carbamates which are obtained by reaction of glycerol carbonate with a primary and/or secondary amine such as, preferably, butylamine, pentylamine, octylamine, decylamine, dodecyl-amine (for example Adogen 163 D from Evonik Goldschmidt, Mapleton, Ill., USA), tetradecylamine, hexadecylamine, octadecylamine, behenylamine, oleylamine (for example Genamin OL 100 D from Clariant), stearylamine (for example Adogen 142 D from Evonik Goldschmidt, Mapleton, Ill., USA), cocoylamine (for example Adogen 160 D from Evonik Goldschmidt, Mapleton, Ill., USA), 2-ethylhexylamine, isotridecylamine, 2-butyloctylamine, 2-hexyldecylamine, 2-octyldodeylarnine, cyclohexylamine, tert. octylamine (for example Primene TOA from Dow), tert. dodecyl/tetradecylamine (for example Primene 81-R from Dow), dibutylamine, dicocoylamine (for example Armeen 2C from Akzo Nobel), di-2-ethylhexylamine, N-methylcyclohexylamine, and, more particularly, dodecylamine, octadecylamine, oleylamine, cocoylamine, and isotridecylamine.

Suitable alkyl and/or alkenyl glycerol carbamates are, for example, the following compounds (only one regioisomer is shown by way of example):

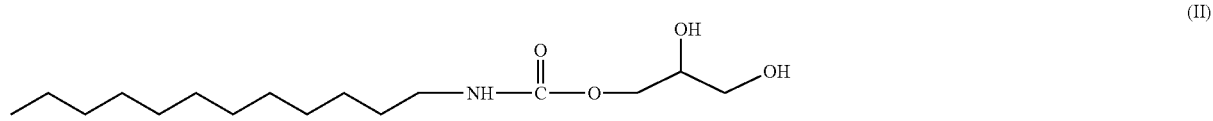

(II)

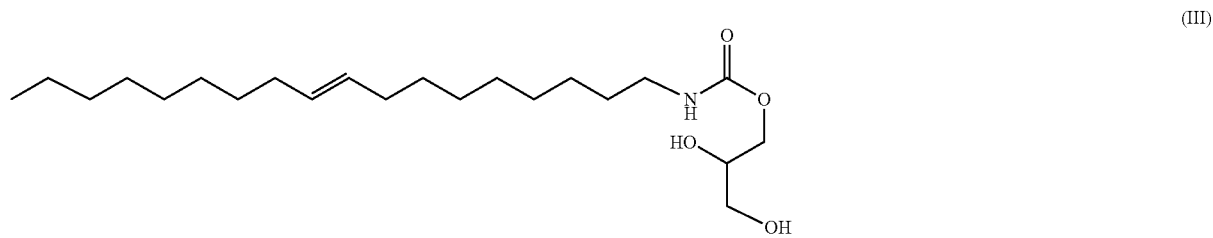

(III)

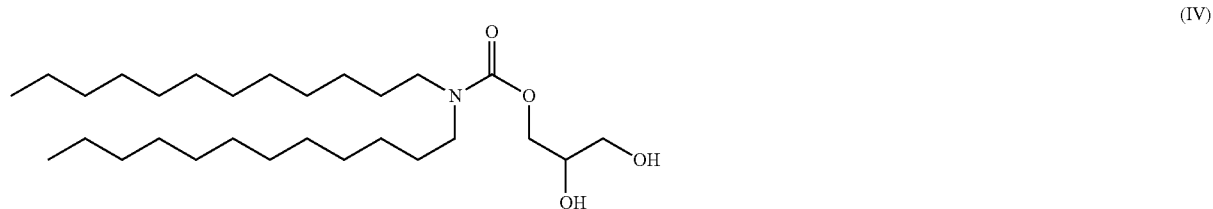

(IV)

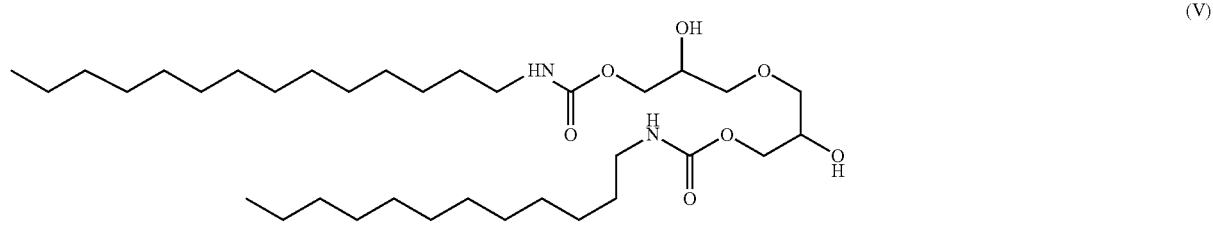

(V)

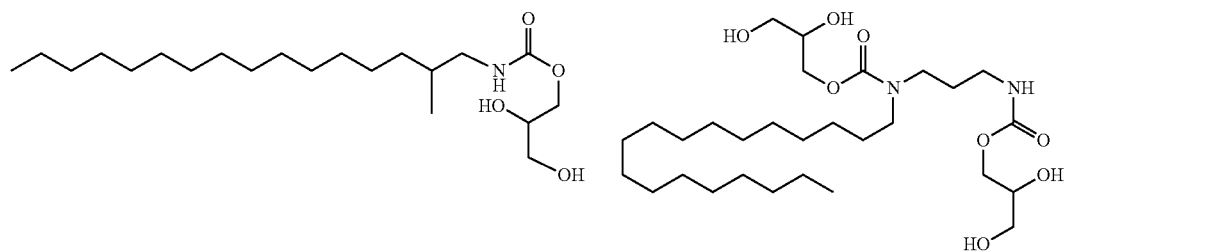

(VI)                                (VII)

-continued

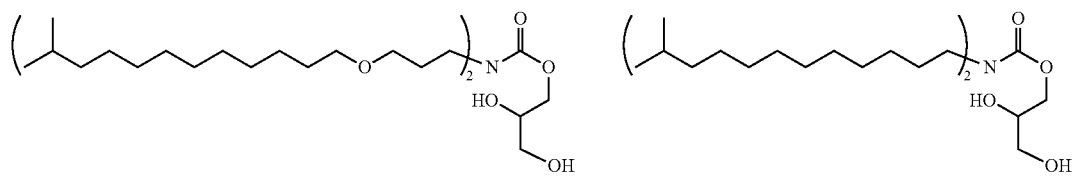

(VIII)

(IX)

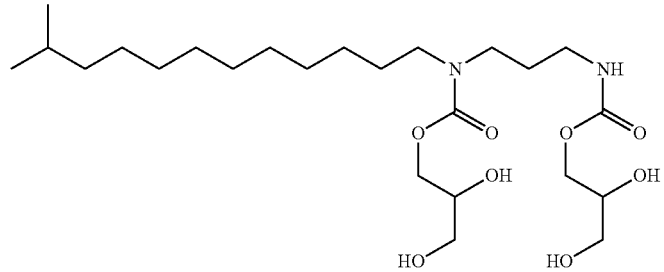

(X)

The alkyl and/or alkenyl glycerol carbamates according to the invention are used in surface-active preparations, preferably in cosmetic and/or pharmaceutical preparations, laundry detergents, dishwashing detergents and cleaners, more particularly in quantities of 0.01 to 20, preferably 0.5 to 10 and more particularly 1.0 to 5.5% by weight, based on the preparations.

A specific embodiment of the invention is characterized by a compound of the Formula A

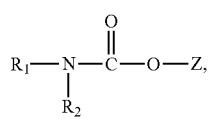

(A)

wherein:
$R_1$ is $(C_8-C_{22})$alkyl, $(C_8-C_{22})$alkenyl, $(C_8-C_{22})$alkynyl, $(C_8-C_{22})$cycloalkyl, $(C_8-C_{22})$arylalkyl, or $—(C_1-C_{22})$alkyl substituted with a $(C_1-C_{13})$alkoxy;
$R_2$ is hydrogen, $(C_8-C_{22})$alkyl, $(C_8-C_{22})$alkenyl, $(C_8-C_{22})$alkynyl, $(C_8-C_{22})$alkyl, $(C_3-C_{22})$arylalkyl, $(C_8-C_{22})$cycloalkyl substituted with a $(C_1-C_{13})$alkoxy, or $(C_1-C_{22})$alkyl substituted with a $(C_1-C_{13})$alkoxy;
Z is:

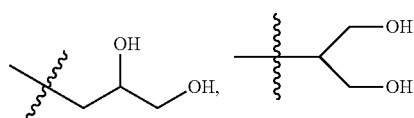

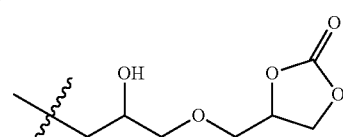

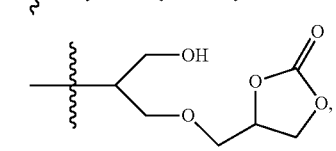

-continued

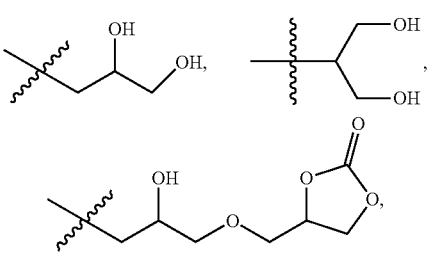

or

A specific embodiment of the invention is characterized by a compound of the Formula B

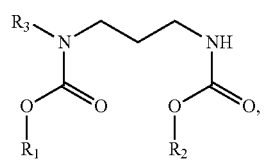

(B)

wherein:
$R_1$ and $R_2$ is

-continued

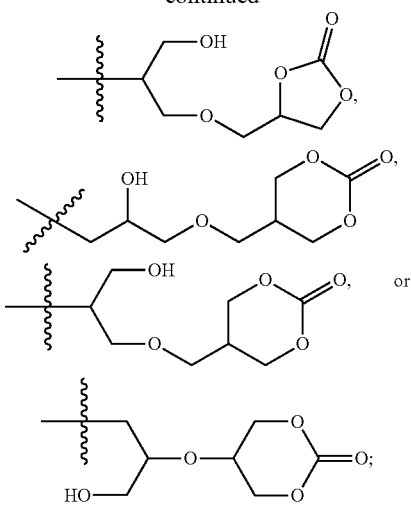

$R_3$ is $(C_8\text{-}C_{22})$alkyl, $(C_8\text{-}C_{22})$alkenyl, $(C_8\text{-}C_{22})$alkynyl, $(C_8\text{-}C_{22})$cycloalkyl, $(C_8\text{-}C_{22})$ arylalkyl, or $(C_1\text{-}C_{22})$ alkyl substituted with a $(C_1\text{-}C_{13})$alkoxy.

A specific embodiment of the invention is characterized by a compound of the Formula C

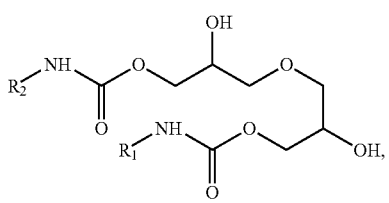
(C)

wherein:

$R_1$ and $R_2$ is $(C_8\text{-}C_{22})$alkyl, $(C_8\text{-}C_{22})$alkenyl, $(C_8\text{-}C_{22})$alkynyl, $(C_8\text{-}C_{22})$cycloalkyl, $(C_8\text{-}C_{22})$arylalkyl, or $(C_1\text{-}C_{22})$alkyl substituted with a $(C_1\text{-}C_{13})$alkoxy.

A particular embodiment of the invention is characterized by isomeric mixtures of the alkyl and/or alkenyl glycerol carbamates of the present invention and the isoforms of the alkyl and/or alkenyl glycerol carbamates of the present invention.

A particular embodiment of the invention is characterized by said isomer mixtures where the weight portion of the alkyl and/or alkenyl glycerol carbamates of the present invention to the isoforms of the alkyl and/or alkenyl glycerol carbamates of the present invention is about 1.1:1 to about 1.8:1.

A specific embodiment of the present invention is characterized by isomeric mixtures of Formula IIA

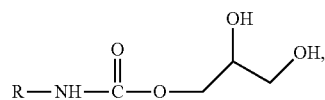
(IIA)

and of the Formula IIB

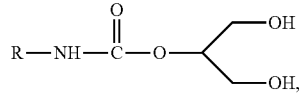
(IIB)

wherein R is $(C_8\text{-}C_{22})$alkyl, $(C_8\text{-}C_{22})$alkenyl, or $(C_8\text{-}C_{22})$alkynyl.

A specific embodiment of the present invention relates to isomer mixtures of 2,3-dihydroxypropyl dodecylcarbamate of the Formula IIC

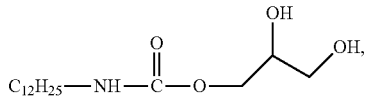
(IIC)

and of 1,3-dihydroxypropan-2-yl dodecylcarbamate of the Formula IID

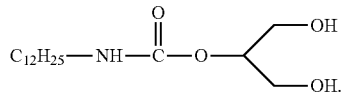
(IID)

A specific embodiment of the present invention is characterized by isomeric mixtures of Formula IIIA

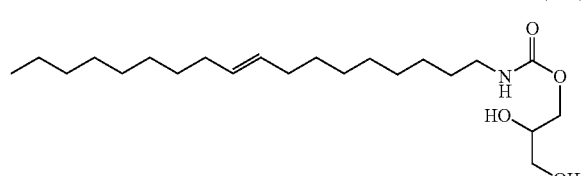
(IIIA)

and of the Formula IIIB

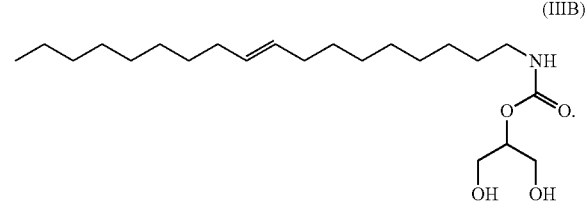 [SMILES: CCCCCCCC/C=C/CCCCCCCCNC(=O)OC(CO)CO]
(IIIB)

A specific embodiment of the present invention is characterized by isomeric mixtures of Formula IVA

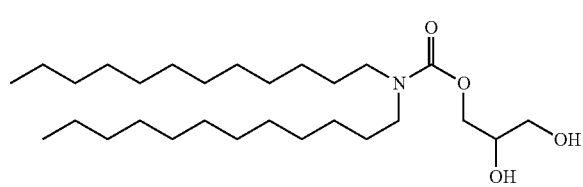
(IVA)

and of the Formula IVB

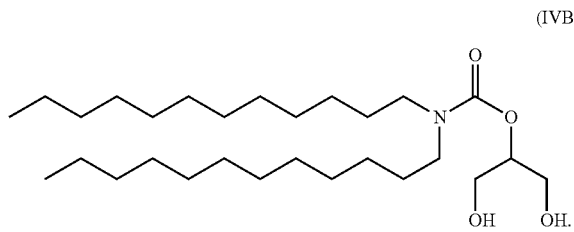
(IVB)

A specific embodiment of the present invention is characterized by isomeric mixtures of Formula VA

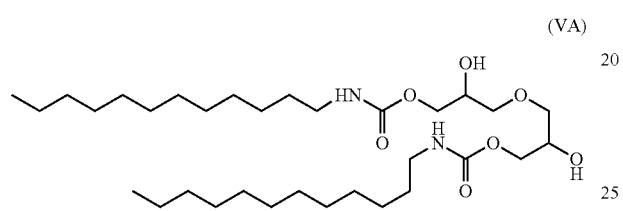
(VA)

and of the Formula VB

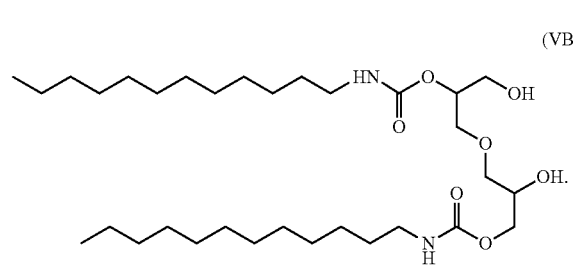
(VB)

A specific embodiment of the present invention is characterized by isomeric mixtures of Formula VIA

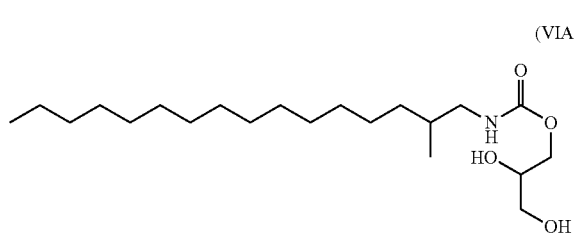
(VIA)

and of the Formula VIB

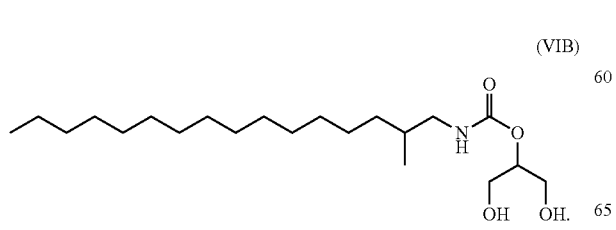
(VIB)

A specific embodiment of the present invention is characterized by isomeric mixtures of Formula VIIA

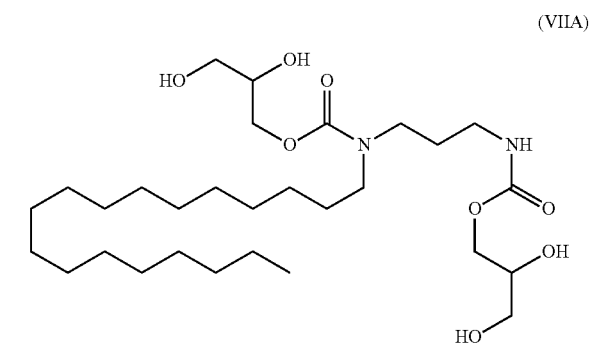 [SMILES: CCCCCCCCCCCCCCCCCCN(CCCNC(=O)OCC(O)CO)C(=O)OCC(O)CO]
(VIIA)

and of the Formula VIIB (VIIB)

A specific embodiment of the present invention is characterized by isomeric mixtures of Formula VIIIA

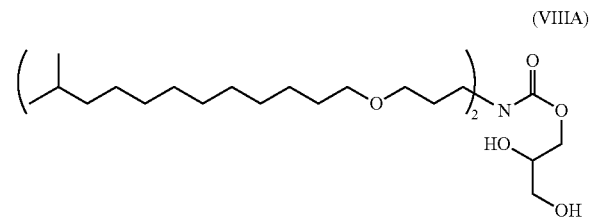
(VIIIA)

and of the Formula VIIIB

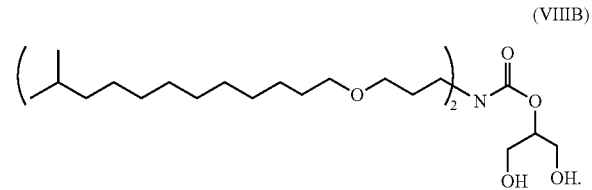
(VIIIB)

A specific embodiment of the present invention is characterized by isomeric mixtures of Formula IXA

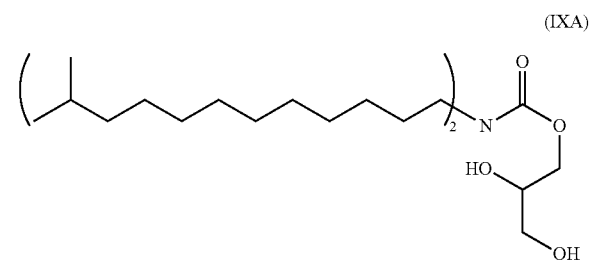
(IXA)

and of the Formula IXB

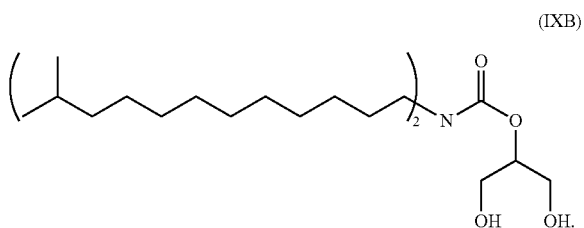

(IXB)

A specific embodiment of the present invention is characterized by isomeric mixtures of Formula XA

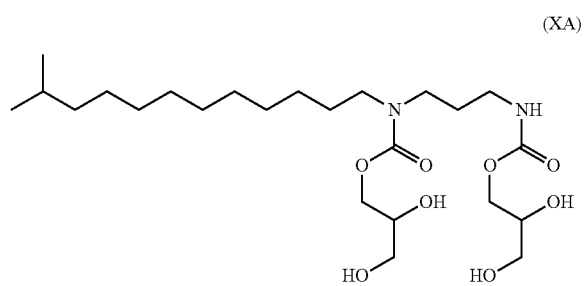 [SMILES: CC(C)CCCCCCCCCCN(CCCNC(=O)OCC(O)CO)C(=O)OCC(O)CO]

(XA)

and of the Formula XB

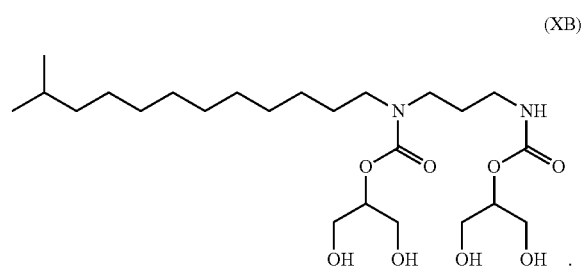 [SMILES: CC(C)CCCCCCCCCCN(CCCNC(=O)OC(CO)CO)C(=O)OC(CO)CO]

(XB)

In one particular embodiment of the invention, the alkyl and/or alkenyl glycerol carbamates according to the invention have a mean crystal size of about 0.1 micron to 500 microns, preferably 1 micron to 200 microns, even more preferably 4 microns to 100 microns.

Production of Alkyl and/or Alkenyl Glycerol Carbamates

The alkyl and/or alkenyl glycerol carbamates according to the invention are obtained by reaction of glycerol, diglycerol and/or polyglycerol carbonate with a primary and/or secondary amine corresponding to Formula (I).

Glycerol, diglycerol and/or polyglycerol carbonate can be produced by methods known from the prior art as described, for example, in patent applications JP 06329663, U.S. Pat. No. 5,091,543, EP 0582201 A1 or EP 0955298 A1 The starting compound used for the synthesis of polyglycerol carbonates is polyglycerol of which the production is described in patent application DE 4029232 A1. Other processes for the production of polyglycerol are disclosed in patent application DE 4117033 A1 or U.S. Pat. No. 5,430,866 .

Glycerol carbonate can be made in many different ways. A comprehensive review was published recently (Sonnati et al., *Glycerol carbonate as a versatile building block for tomorrow: synthesis, reactivity, properties and applications*, Green Chemistry, 15, 283-306, 2013). For example, glycerol carbonate can be obtained by base-catalyzed (for example 1 mol-% NaOMe) transesterification of 1 mol glycerol with 1.6 mol dimethyl carbonate at ca. 70 to 80° C. and removal of the methanol formed and excess DMC by distillation as described in U.S. Pat. No. 5,091,543. Glycerol carbonate can also be prepared by reaction of glycerol and urea with Lewis acids catalysts. For example, metal sulfate catalysts were described in U.S. Pat. No. 6,025,504. Zinc oxide catalysts were described in Japanese Patent No. 2007/039347. Selection of solvents for conversion of urea and glycerol to carbonates was described in European Patent Publication No. 2,174,937. Another way to synthesize glycerol carbonate in a more environmentally friendly way is by transcarbonation of dimethyl carbonate and glycerol. Recently, enzyme technology has shown promising conversion of dimethyl carbonate and glycerol to glycerol carbonates (WO Patent Publication No., WO2009/035269).

Diglycerol carbonate is obtained by reaction of 1 mol diglycerol (TCI America Catalog, Number T01 19, 80% purity) with 3.2 mol dimethyl carbonate as described above.

Polyglycerol carbonate is preferably obtained by reaction of polyglycerol-4 (Solvay S. A.) with an excess of dimethyl carbonate as described above.

To produce the alkyl and/or alkenyl glycerol carbamates of this invention, glycerol carbonate was placed in a vessel. Amine was added to the glycerol carbonate solution and the mixture was heated to 50-90° C. The amine is preferably a fatty amine with saturated or unsaturated alkyl radical, linear or branched, with 8 to 22 carbons. The molar ratio of the amine to the glycerol carbonate is preferably about 0.7-1:3 to 1. The reaction was then cooled down to room temperature. The alkyl and/or alkenyl glycerol carbamates according to the invention may be used as such without any further work up.

Commercial Applications

The glycerol carbamates according to the invention may be used in surface-active preparations. Surface-active preparations in the context of the invention are preferably cosmetic and/or pharmaceutical preparations, laundry detergents, dishwashing detergents and household cleaners. Besides the carbamates according to the invention, these surface-active preparations may contain other known ingredients typical of the particular application in the usual concentrations. The total percentage content of the typical ingredients may be in the range from 1 to 80, preferably 5 to 50 and more particularly 7 to 10% by weight, based on the preparation.

Preferred cosmetic preparations are hair shampoos, hair lotions, foam baths, shower baths, creams, gels, lotions, alcoholic and aqueous/alcoholic solutions and emulsions which may contain conditioners, salts, thickeners, emulsifiers, emollients, active ingredients, superfatting agents, stabilizers, silicone compounds, fats, waxes, lecithins, phospholipids, antioxidants, deodorants, antiperspirants, antidandruff agents, swelling agents, tyrosine inhibitors, hydrotropes, solubilizers, preservatives, perfume oils, dyes, other surfactants and the like as further auxiliaries and additives. The total percentage content of the auxiliaries and additives may be in the range from 1 to 80, preferably 5 to 50 and more particularly 7 to 10% by weight, based on the preparation. The preparations may be produced by standard cold or hot emulsification or by the PIT process.

Suitable surfactants include, but are not limited to, sodium lauryl sulfate, sodium laureth sulfate, sodium dodecyl sulfate, sodium cocoyl sulfate, ammonium lauryl sulfate, ammonium laureth sulfate, triethylamine lauryl sulfate, triethylamine laureth sulfate, triethanolamine lauryl sulfate, triethanolamine laureth sulfate, monoethanomine lauryl sulfate, monoethanolamine laureth sulfate, diethanolamine laurylsulfate, diethanolamine laureth sulfate, potassium lauryl sulfate, potassium laureth sulfate, potassium cocoyl sulfate, sodium tetradecyl sulfate, sodium lauryl sarcosinate, sodium dodecyl benzene sulfonate, sodium cocoamphoacetate, disodium cococamphodiacetate, sodium sulfocuccinate, sodium cocoamphoprionates, sodium lauroamphodiacetates, sodium cocoyl taurates, sodium cocoyl sarcosinate, sodium cocoyl sulfoacetate, sodium cocoyl glutamate, sodium cocoyl glycinates, capryl/capramidopropyl betain, cocamidopropyl betain, coco-betain, lauramidopropyl betain, decyl betain, cetyl betain, myristyl betain, myristamidopropyl betain, oleyl betain, isostearylamidopropyl betain, behenyl betain, behenamidopropyl betain, babassuamidopropyl betaine, shea butter amidopropyl betain, almondamidopropyl betain, coca-sultan, coco-hydroxysultain, lauramidopropyl hydroxysultain, cocamidopropyl hydroxysultain, decyl glucoside, coco glucoside, hexadecyl glucoside, lauryl glucoside, other glucoside surfactants, ethoxylated fatty alcohols such as laureth-4, laureth-6, laureth 7, laureth-10, laureth-20, and ceteareth-25.

Suitable salts include, but are not limited to, sodium chloride, sodium acetate, magnesium chloride, potassium chloride, and sodium citrate.

Suitable thickeners include, but are not limited to, cocamide MEA, cocamide DEA, cocamide MIPA, lauramide MEA, lauramide DEA, lauramide MIPA, isosteamide MIPA, PEG-150 distearate, PEG-120 methyl glucose dioleate, PEG-18 glyceryl oleate/cocoate, PEG-200 hydrogenated glyceryl palmate, hydroxypropyl methylcellulose, natural polymers such as xanthum gum, guar gum, and synthetic polymers such as carbomers, and acrylate/C10-30 alkyl acrylate copolymer.

Suitable emulsifiers include, but are not limited to, cetyl PEG/PEG-10/1 dimethicone, bis-PEG/PPG-14/14 dimethicone, Ns-PEG/PPG-16/16 PEG/PPG-16/16 dimethione, bis-PEG/PPG-20/5 PEG/PPG-20/5 dimethicone, glycerine or sugar-based, such as polyglyceryl-4 isostearate, polyglyceryl-3 oleate, polyglycer-4 diisostearate/polyhydroxystearate/sebacate, methyl glucose isostearate, diisostearoyl polyglycerl-3-dimmer dilinoleate, glyceryl oleate, sorbitan laurate, sorbitan oleate, sorbitan stearate, sorbitan trioleate, cetearyl glucoside, polyglyceryl-4 laurate, methyl glucose sesquisterate, and glycol stearate.

Suitable emollients include, but are not limited to, cyclopentasilocane, isoamyl cocoate, diethylhexyl carbonate, isopropyl myristate, isopropyl palmitate, decyl cocoate, ethylhexyl palmitate, phenoxyethyl caprylate, $C_{12}$-$C_{15}$ alkyl benzoate, ethylhexylstearate, cetyl ethylhexanoate, decyl oleate, cetearyl isononaoate, caprylic/capric triglyceride, cetyl dimethicone, PPG-3 myristayl ether, oleyl erucate, dimethicone, natural oils such as avocado oil, argan oil, jojoba oil, and tea tree oil.

Suitable active ingredients include, but are not limited to vitamins such as tocopheryl acetate (vitamin E), ascorbic acid (vitamin C), and panthenoic acid (Vitamin B5), amino acids such as lysine, glycine, alanine, arginine, serine, aspartic acid, cystine, leucine, and tyrosine, botanical extracts, hydrolyzed proteins, ceramide, phytosphingosine, and creatine.

The compounds according to the invention may advantageously be used as pearlizing agents in surface-active preparations. Accordingly, the present invention also relates to the use of the alkyl and/or alkenyl glycerol carbamates according to the invention as pearlizing agents in surface-active preparations, preferably in cosmetic and/or pharmaceutical preparations, laundry detergents, dishwashing detergents and household cleaners.

Cosmetic and/or pharmaceutical preparations, laundry detergents, dishwashing detergents and household cleaners and, more particularly cosmetic preparations, containing the carbamates according to the invention, preferably as pearlizing agents, in quantities of 0.01 to 10, preferably 0.5 to 8 and more particularly 1.0 to 5.5% by weight, based on the preparations, preferably have Brookfield viscosities in the range from 2,000 to 300,000, more preferably in the range from 3,000 to 100,000 and most preferably in the range from 4,000 to 25,000 cps (25° C., 20 r.p.m., spindle 5).

In one particular embodiment of the invention, the compounds according to the invention are used as pearlizing agents in the above-mentioned concentrations in cosmetic and/or pharmaceutical microemulsions Typical cosmetic and/or pharmaceutical cleaning preparations preferably have the following composition:

(a) 0.01 to 10, preferably 0.5 to 8 and more particularly 1.0 to 5.5% by weight of the alkyl and/or alkenyl glycerol carbamates according to the invention and (b) 3 to 30, preferably 5 to 20 and more particularly 10 to 15% by weight surfactants, with the proviso that the quantities shown add up to 100% by weight with water and optionally other auxiliaries and additives.

Typical cosmetic and/or pharmaceutical emulsions preferably have the following composition;

(a) 0.01 to 10, preferably 0.5 to 8 and more particularly 1.0 to 5.5% by weight alkyl and/or alkenyl glycerol carbamates, (b) 3 to 30, preferably 5 to 20 and more particularly 10 to 15% by weight oil components and (c) 1 to 30, preferably 3 to 20 and more particularly 5 to 10% by weight surfactants, with the proviso that the quantities shown add up to 100° by weight with water and optionally other auxiliaries and additives.

In one particular embodiment of the invention, the composition has a viscosity range of about 2,000 to 200,000 cps, preferably 5,000 to 150,000 cps.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The pearlizing agents according to the invention were tested in eight different basic formulations which had the following compositions:

Example 1

A shampoo formulation was prepared as follows:

| | |
|---|---|
| Sodium laureth sulfate | 32 |
| Cocamidopropyl betain | 7.9 |
| Water | 57.6 |
| Sodium chloride | 1.0 |
| N-laurylhydroxyurethane | 1.5 |

Sodium laureth sulfate (28%, Standapol® ES-2, BASF Corporation), cocamidopropyl betain (36%, Tego® Betain F 50, Evonik Goldschmidt Corporation), water and sodium chloride were mixed and heated to 70-80° C. N-laurylhydroxyurethane was then added. The solution was stirred until it became clear. The shampoo was cooled down to room temperature, and the pH was adjusted to 5.0-5.5.

The formulation displays a shiny, pearlescent appearance. The formulation also showed a significantly higher viscosity. Without the addition of N-laurylhydroxyurethane the shampoo viscosity was 80 cps. With the addition of N-laurylhydroxyurethane the viscosity was 12,800 cps.

Comparative Example 1

A shampoo formulation was prepared as follows:

| | |
|---|---|
| Sodium laureth sulfate | 32 |
| Cocamidopropyl betain | 7.9 |
| Water | 57.6 |
| Sodium chloride | 1.0 |
| Glycol distearate | 1.5 |

Sodium laureth sulfate (28%, Standapol® ES-2, BASF Corporation), cocamidopropyl betain (36%, Tego® Betain F 50, Evonik Goldschmidt Corporation), water and sodium chloride were mixed and heated to 70-80° C. Glycol distearate was then added. The solution was stirred until it became clear. The shampoo was cooled down to room temperature, and the pH was adjusted to 5.0-5.5.

This formulation resulted in a white emulsion with no pearlescent effect. The viscosity of the formulation was also zero.

Example 2

A polyethylene glycol (PEG), sulfate free shampoo formulation was prepared as follows:

| | |
|---|---|
| Lauryl glucoside | 8.6 |
| Cocoyl glucoside | 3.2 |
| Cocamidopropyl betain | 14.6 |
| Water | 60.0 |
| Sodium cocoamphoacetate | 11.1 |
| Sodium chloride | 1.0 |
| N-laurylhydroxyurethane | 1.5 |

Lauryl glucoside (50-53%, Plantacare® 1200, BASF Corporation), cocoyl glucoside (51-53%, Plantacare® 818, BASF Corporation), cocamidopropyl betain (36%, Tego® Betain F 50, Evonik Goldschmidt Corporation), water, sodium cocoamphoacetate (33%, Rewoteric® AMC, Evonik Goldschmidt Corporation) and sodium chloride were mixed and heated to 70-80° C. N-laurylhydroxyurethane was then added. The solution was stirred until it became clear. The shampoo was cooled down to room temperature, and the pH was adjusted to 5.0-5.5.

The formulation displays a shiny, pearlescent appearance. The formulation also showed a significantly higher viscosity. Without the addition of N-laurylhydroxyurethane the shampoo does not have viscosity. With the addition of N-laurylhydroxyurethane the viscosity was 1040 cps.

Example 3

A conditioning shampoo formulation was prepared as follows:

| | |
|---|---|
| Palmitoamidopropylammonium chloride | 2.3 |
| Disodium laurylsulfosuccinate | 3.8 |
| Cocamidopropyl betain | 10.0 |
| Water | 66.4 |
| Sodium cocoamphoacetate | 15.0 |
| Sodium chloride | 1.0 |
| N-laurylhydroxyurethane | 1.5 |

Palmitoamidopropylammonium chloride (Varisoft® PATC, Evonik Goldschmidt Corporation), disodium laurylsulfosuccinate (40%, Rewopol® FB SB 12 P, Evonik Goldschmidt Corporation) cocamidopropyl betain (36%, Tego® Betain F 50, Evonik Goldschmidt Corporation), water, sodium cocoamphoacetate (33%, Rewoteric® AM C, Evonik Goldschmidt Corporation) and sodium chloride were mixed and heated to 70-80° C. N-laurylhydroxyurethane was then added. The solution was stirred until it became clear. The shampoo was then cooled down to room temperature, and the pH was adjusted to 5.0-5.5.

The formulation displays a shiny, pearlescent appearance. The formulation also showed a significantly higher viscosity. Without the addition of N-laurylhydroxyurethane the shampoo viscosity was 120 cps. With the addition of N-laurylhydroxyurethane the viscosity was 9,720 cps.

Example 4

A shampoo formulation with other rheological additives was prepared as follows:

| | |
|---|---|
| Phase A | |
| Sodium laureth sulfate | 32 |
| N-laurylhydroxyurethane | 1.5 |
| Coco-betain | 9.8 |
| Water | 54.4 |
| Dimethicone | 0.5 |
| Sodium chloride | 0.5 |
| Phase B | |
| Isopropyl palmitate | 0.6 |
| Carbomer | 0.2 |
| Phase C | |
| Sodium hydroxide (30%) | 0.5 |

Phase A preparation: Sodium laureth sulfate (28%, Standapol® ES-2, BASF Corporation), coco-betain (31%, Tego Betain AB 1214, Evonik Goldschmidt Corporation), water, dimethicone (Abil® 350, Evonik Goldschmidt Corporation), N-laurylhydroxyurethane and sodium chloride were mixed and heated to 75° C.

Phase B preparation: Carbomer (Tego® Carbomer 141, Evonik Goldschmidt Corporation) was dissolved in isopropyl palmitate (Tegosoft® P, Evonik Goldschmidt Corporation).

Phase B was added to Phase A at 60° C. The formulation was homogenized. Phase C was added at 40° C.

The shampoo displayed a pearlescent appearance with a viscosity of 10,040 cps.

Example 5

A shampoo formulation with natural conditioner was prepared as follows:

| | |
|---|---|
| Sodium laureth sulfate | 32 |
| N-laurylhydroxyurethane | 1.5 |
| Cocamidopropylbetain | 7.9 |
| Water | 56.7 |
| Dimethicone | 0.5 |
| Sodium chloride | 0.5 |
| Guar hydroxypropyltrimonium chloride | 0.3 |
| Tetrasodium EDTA | 0.3 |

Sodium laureth sulfate (28%, Standapol® ES-2, BASF Corporation), cocamidopropyl betain (36%, Tego® Betain F 50, Evonik Goldschmidt Corporation), water, dimethicone (Abil® 350, Evonik Goldschmidt Corporation), sodium chloride, guar hydroxypropyltrimonium chloride (Jaguar® C1000, Rhodia Corporation), N-laurylhydroxyurethane, were mixed in the above chronological order. The mixture was heated to 75° C. and then cooled down to room temperature. The shampoo displayed a pearlescent appearance with a viscosity of 8,260 cps.

Example 6

A pearlized liquid soap was prepared as follows:

| | |
|---|---|
| Sodium laureth sulfate | 40.0 |
| Sucrose cocoate | 3.0 |
| Water | 49.1 |
| Cocamidopropyl betain | 6.4 |
| N-laurylhydroxyurethane | 1.5 |

Sodium laureth sulfate (28%, Standapol® ES-2, BASF Corporation), cocamidopropyl betain (36%, Tego® Betain F 50, Evonik Goldschmidt Corporation), sucrose cocoate (65%, Tegosoft® LSE 65 K SOFT, Evonik Goldschmidt Corporation) and water were mixed and heated to 70-80° C. N-laurylhydroxyurethane was then added. The solution was stirred until it became clear. The formulation was cooled down to room temperature.

The hand soap displayed an excellent pearlescent appearance. Viscosity was 8,280 cps.

Example 7

A body wash was prepared as follows:

| | |
|---|---|
| Sodium laureth sulfate | 32.0 |
| Cocamidopropyl betain | 8.2 |
| Water | 55.6 |
| Decyl Glucoside | 1.4 |
| Sodium chloride | 1.0 |
| N-laurylhydroxyurethane | 1.5 |
| Tetrasodium EDTA | 0.3 |

Sodium laureth sulfate (28%, Standapol® ES-2, BASF Corporation), Cocamidopropyl betain (36%, Tego® Betain F 50, Evonik Goldschmidt Corporation), Decyl Glucoside (51-55%, Plantacare® 2000, BASF Corporation), water and sodium chloride were mixed and heated to 70-80° C. N-laurylhydroxyurethane was then added. The solution was stirred until it became clear. The formulation was cooled down to room temperature. Tetrasodium EDTA was added.

The body wash displayed a pleasant, pearlescent appearance with a viscosity of 11,340 cps.

Example 8

A shampoo for fine hair was prepared as follows:

| | |
|---|---|
| Sodium laureth sulfate | 32.0 |
| Cocamidopropyl betain | 8.2 |
| Water | 55.6 |
| Guar hydroxypropyltrimonium chloride | 0.1 |
| Sodium chloride | 0.7 |
| N-laurylhydroxyurethane | 1.5 |
| Hydrolyzed wheat protein | 5.0 |
| Preservatives | 0.3 |

Guar hydroxypropyltrimonium chloride (Jaguar C-13 S, Rhodia) was dispersed in water. pH was adjusted to 4.37 with citric acid. Sodium laureth sulfate, cocamidopropyl betain and sodium chloride were added and mixed. Formula was heated to 75° C. N-laurylhydroxyurethane was added and heated at 400 rpm for 15 minutes. Formula was cooled down to 40° C. Hydrolyzed wheat protein (Jeechem 100 WP) and preservatives were added below 40° C.

The shampoo has a pearlescent appearance with viscosity of 12,200 cps.

Example 9

A silky cationic body cream was prepared as follows:

| | |
|---|---|
| Phase A | |
| Bis-PEG/PPG-20/5 PEG/PPG-20/5 dimethicone, methoxy PEG/PPG-25/4 dimethicone, caprylic/capric triglyceride | 1.0 |
| Distearyldimonium chloride | 2.0 |
| N-laurylhydroxyurethane | 2.0 |
| Stearyl alcohol | 1.5 |
| Cetearyl ethylhexanoate | 9.0 |
| Caprylic/capric triglyceride | 9.0 |
| Phase B | |
| Glycerine | 3.0 |
| Water | 72.5 |

Phase A preparation: Bis-PEG/PPG-20/5 PEG/PPG-20/5 dimethicone, methoxy PEG/PPG-25/4 dimethicone, caprylic/capric triglyceride (Abil® care XL 80, Evonik Goldschmidt Corporation), distearyldimonium chloride (Varisoft®TA 100, Evonik Goldschmidt Corporation), N-laurylhydroxyurethane, stearyl alcohol (Tego® Alkanol 18, Evonik Goldschmidt Corporation), cetearyl ethylhexanoate (Tegosoft® Liquid, Evonik Goldschmidt Corporation), and caprylic/carpric triglyceride (Tegosoft® CT, Evonik Goldschmidt Corporation) were mixed and heated to 70-75° C. Separately, phase B was heated separately to 70-75° C. Phase A was added to Phase B with stirring. The mixture was homogenized. The formulation was cooled down to room temperature with gentle stirring.

The cream displayed a pleasant pearlescent appearance. Viscosity was 2,120 cps.

TABLE 1

| Sample | Dodecylamine | Residual amine by Titration, % | Glycerol Starting Material | Glycerine carbonate | Major peak ratio | | Third peak |
|---|---|---|---|---|---|---|---|
| 1 | 0.24 | 1.9 | 6.1 | 1.28 | 34.56 | 47.71 | 10.56 |
| 2 | 0.19 | 1.6 | 5.2 | 1.53 | 33.49 | 48.49 | 11.93 |

Sample preparation: Dodecylamine (Adogen 163 D, Evonik Goldschmidt Corporation) was added to glycerol carbonate (Jeffsol G C, Hunstman Corporation) in a vessel. The reaction mixture was heated to 50-90° C. The reaction was then cooled down to room temperature. Product is a white solid with melting temperature of 50-55° C. The products that resulted from the reaction in Sample 1 and Sample 2 by following the above procedure were analyzed using gas chromatography. Ratio of the isomer of Formula IIC and Formula IID was calculated based on the area of the major peak ratio. For sample 1, the isomer ratio is calculated as 47.71:34.56=1.38:1. For sample 2, the isomer ratio is calculated as 48.49:33.49=1.45:1. The gas chromatography result show that the ratio of the isomer of Formula IIC and Formula IID was 1.38-1.45:1. Major peaks and third peak are reported as total peak area %.

TABLE 2

Crystal size of the examples (in microns)

| | Mean Diameter | Medium Diameter | Standard Deviation | D10 | D90 |
|---|---|---|---|---|---|
| Example 1 | 18.71 | 16.21 | 12.41 | 4.69 | 36.89 |
| Example 2 | 24.20 | 15.62 | 23.95 | 4.90 | 61.07 |
| Example 3 | 5.46 | 5.05 | 3.12 | 1.81 | 9.88 |
| Example 4 | 41.77 | 38.80 | 26.45 | 9.89 | 79.08 |
| Example 5 | 14.05 | 12.25 | 9.34 | 3.92 | 26.59 |
| Example 6 | 16.74 | 15.55 | 9.08 | 6.28 | 29.11 |
| Example 7 | 12.55 | 11.45 | 7.69 | 4.16 | 21.94 |
| Example 8 | 11.83 | 17.04 | 7.27 | 5.55 | 21.71 |

What is claimed is:

1. The pearlizing agent is an isomer mixture of 2,3-dihydroxypropyl dodecylcarbamate of the Formula IIC

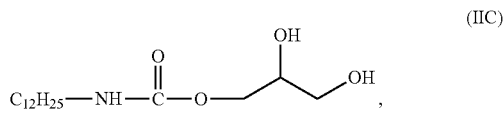

(IIC)

and of 1,3-dihydroxypropan-2-yl dodecylcarbamate of the Formula IID

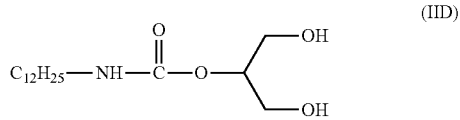

(IID)

wherein the mean crystal size of the pearlizing agent is about 1 to 200 microns.

2. The pearlizing isomer mixture according to claim 1, wherein the weight portion of 2,3-dihydroxypropyl dodecylcarbamate (IIC) to 1,3-dihydroxypropan-2-yl dodecylcarbamate (IID) is about 1.1:1 to about 1.8:1.

3. A pearlizing composition comprising a mixture of:
(a) 0.01 to 10% by weight of the pearlizing agent according to claims 1;
(b) 3 to 30% by weight of a surfactant,
with the proviso that the quantities add up to 100% by weight with water and optionally other auxiliaries and additives.

4. A pearlizing composition comprising a mixture of:
(a) 0.01 to 10% by weight of the pearlizing agent according to claims 1;
(b) 3 to 30% by weight of oil components; and
(c) 3 to 30% by weight of surfactants,
with the proviso that the quantities add up to 100% by weight with water and optionally other auxiliaries and additives.

5. The pearlizing composition of claim 3, wherein the surfactant comprises sodium lauryl sulfate, sodium laureth sulfate, sodium dodecyl sulfate, sodium cocoyl sulfate, ammonium lauryl sulfate, ammonium laureth sulfate, triethylamine lauryl sulfate, triethylamine laureth sulfate, triethanolamine lauryl sulfate, triethanolamine laureth sulfate, monoethanomine lauryl sulfate, monoethanolamine laureth sulfate, diethanolamine laurylsulfate, diethanolamine laureth sulfate, potassium lauryl sulfate, potassium laureth sulfate, potassium cocoyl sulfate, sodium tetradecyl sulfate, sodium lauryl sarcosinate, sodium dodecyl benzene sulfonate, sodium cocoamphoacetate, disodium cococamphodiacetate, sodium sulfocuccinate, sodium cocoamphoproprionates, sodium lauroamphodiacetates, sodium cocoyl taurates, sodium cocoyl sarcosinate, sodium cocoyl sulfoacetate, sodium cocoyl glutamate, sodium cocoyl glycinates, capryl/capramidopropyl betain, cocamidopropyl betain, coco-betain, lauramidopropyl betain, decyl betain, cetyl betain, myristyl betain, myristamidopropyl betain, oleyl betain, isostearylamidopropyl betain, behenyl betain, behenamidopropyl betain, babassuamidopropyl betaine, shea butter amidopropyl betain, almondamidopropyl betain, coco-sultain, coco-hydroxysultain, lauramidopropyl hydroxysultain, cocamidopropyl hydroxysultain, decyl glucoside, coco glucoside, hexadecyl glucoside, lauryl glucoside, laureth-4, laureth-6, laureth 7, laureth-10, laureth-20, ceteareth-25, or a mixture thereof.

6. A pearlizing composition of claim 3 where the viscosity is in the range of about 2,000-200,000 cps.

7. A method of preparing a pearlizing agent of claim 1 comprising: 1) the addition of a fatty amine with saturated or unsaturated alkyl radical, linear or branched, with 8 to 22 carbons to glycerol carbonate where the molar ratio of the fatty amine to the glycerol carbonate is 0.7-1:3 to 1; 2) heating the reaction mixture to 50-90° C.; and 3) cooling down the reaction to room temperature.

* * * * *